(12) United States Patent
Le Febre et al.

(10) Patent No.: US 6,333,088 B1
(45) Date of Patent: Dec. 25, 2001

(54) COMPOUND CAPILLARY ASSEMBLY AND USE IN SEPARATIVE TRANSPORT

(75) Inventors: David A. Le Febre, Camino; Roy V. Semerdjian, Sacramento; Thomas B. Martin, Jr., Placerville, all of CA (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/231,336

(22) Filed: Jan. 13, 1999

(51) Int. Cl.[7] .............................. B22D 22/00; B01D 33/21
(52) U.S. Cl. ................. 428/36.91; 428/36.9; 210/500.23
(58) Field of Search .......................... 428/36.9, 36.91, 428/34.1, 34.4, 34.5, 425.6, 428; 96/101; 95/83; 210/500.23

(56) References Cited

U.S. PATENT DOCUMENTS

| | | |
|---|---|---|
| Re. 34,757 | 10/1994 | Smith et al. ................. 204/299 R |
| 3,531,919 | * 10/1970 | Ignatius et al. ................. 55/386 |
| 4,107,041 | * 8/1978 | Karlson ................. 210/198 |
| 4,293,415 | 10/1981 | Bente, III et al. ................. 210/198.2 |
| 4,650,964 | * 3/1987 | Vincent ................. 219/301 |
| 5,045,172 | 9/1991 | Guzman ................. 204/299 R |
| 5,082,700 | * 1/1992 | Dwivedi ................. 428/34.4 |
| 5,202,010 | 4/1993 | Guzman ................. 204/299 R |
| 5,382,458 | * 1/1995 | Dwivedi ................. 428/34.4 |
| 5,552,042 | 9/1996 | Le Febre et al. ................. 210/198.2 |
| 5,649,043 | * 7/1997 | Adams et al. ................. 385/110 |
| 5,653,777 | 8/1997 | Semerdjian ................. 65/17.2 |
| 5,692,078 | 11/1997 | Le Febre ................. 385/6 |
| 5,882,510 | * 3/1999 | Basse et al. ................. 210/150 |

OTHER PUBLICATIONS

Lewis, Richard, Sr., Hawley's Condensed Chemical Dictionary, 13th ed., John Wiley and Sons, Inc, p. 231, 1997.*

* cited by examiner

Primary Examiner—Rena L. Dye
Assistant Examiner—Michael Miggins
(74) Attorney, Agent, or Firm—John G. Tolomei; James C. Paschall

(57) ABSTRACT

A compound capillary can provide different sizes and configurations for central and outer passages to suit a variety of process applications, in particular methods of separative transport of multi-component samples and precise heat control of fluid streams on a micro scale. The compound capillary can be formed from ductile glass material into an assembly that typically provides a central passageway for retaining one fluid or material and single or multiple outer passages for retaining different fluids or materials. One or more of the different passages may also retain one more different stationary phase to tailor the separative transport to the material of particular sample streams. The compound capillary has particular application to the field of capillary electrophoresis where the multiple capillary passages in a single capillary tube may be used to increase sample through, or used for different function such as cooling and/or the establishment of transverse electrical potentials.

16 Claims, 3 Drawing Sheets

COMPOUND CAPILLARY ASSEMBLY AND USE IN SEPARATIVE TRANSPORT

FIELD OF THE INVENTION

This invention relates to capillary assemblies especially useful in separative transport such as electrophoresis and gas solid partition chromatography. In particular, the invention relates to a single conduit that contains multiple capillary sized passages.

BACKGROUND OF THE INVENTION

The term capillary structures as used in this invention generally refers to tubes with small bores made of amorphous materials such as quartz or fused silica. U.S. Pat. No. 293,415 teaches the use of silica capillary columns for gas chromatography and teaches manufacturing in much the same way as the production of hollow optical fibers. It is also known from U.S. Pat. No. 5,552,042 to wind silica capillaries on open tubular assemblies such as a fused mandrel to provide, after annealing, a relatively stress-free rigid winding.

Capillary structures are also used in electrophoresis. Electrophoresis methods generally place oppositely charged electrodes at opposite ends of an ionic base to provide an electric field. The applied electric field produces a migration of electrons through the ionic solution that separates a sample as it is dragged along with the migrating charge in the direction of the cathode. General methods for practicing electrophoresis are well known and are briefly described in the text entitled "Practical Capillary Electrophoresis". Capillary electrophoresis (CE) retains the ionic solution, or buffer as it is often called, in the bore of a capillary and places the oppositely charged electrodes at opposite ends of the capillary. As the mobile positive charges migrate through the buffer in the direction of the cathode, sample is again dragged along with the migrating charge through the ionic solution or buffer. Basic capillary electrophoresis is also referred to as capillary zone electrophoresis (CZE). A number of the electrochemical mechanisms may be employed in conjunction with CZE and the use of the term capillary electrophoresis (CE) in this invention is meant to refer generally to any arrangement where an electrical field drives solutes through a capillary or arrangement that uses an electroosmotic flow to separate or isolate components. Types of methods falling in this definition include: capillary isoelectric focusing (CIEF) that uses carrier ampholytes to create a pH gradient through the capillary; Capillary Gel Electrophoresis (CGE) where the capillary passage retains an ionic gel; Capillary Isotachophoresis (CITP) that normalizes the velocity of the sample components through the capillary; Electrokinetic Capillary Chromatography (EKC) that employs a semi-stationary phase in a background electrolyte; and Capillary Electrochromatography (CEC) that employs electroosmotic pumping. Additional information and arrangements for capillary electrophoresis can be generally found in patents such as U.S. Pat. No. 5,045,172 and RE34,757.

Whether used in chromatographic separations or capillary electrophoresis, capillary structures have generally consisted of a single uniform capillary. In some applications, individual capillaries may be grouped together to provide simultaneous sampling. The use of multiple capillaries to analyze single samples presents numerous problems in the handling of multiple thin capillary members along with making connections to capillaries that should simultaneously receive and deliver samples from the small openings of the capillaries.

The only structure that resembles multiple capillaries has been used in image intensifiers. Image intensifiers, also known as a night vision scopes, use a structure comprising bundles of fibers. The method for manufacturing the fiber bundle for a night vision scope draws a circular glass tube through a hex die. The resultant hex shaped tubes with circular holes are then grouped together and drawn together as an assembly to form a fused bundle of reduced cross-section. The external hex shape of individual capillaries facilitates the packing together of a grouping of capillaries., i.e. similar to a bee's honeycomb. It is also known in the art to make a multi-passage capillary assembly with this arrangement by using hollow tubes instead of fibers. The circular holes in such a bundle are ordered with no void space in the walls and the assembly can become very large. A variation of this method casts each starting hexagonal member instead of die drawing. The biggest disadvantage to this approach is the resultant final shape of the assembly which is a hex. In many applications, such as a gas chromatograph, the ends of the multi-capillary need to be attached to other parts; the hex shape causes difficulties in getting compression type fittings to interface.

The problem of making connections to capillary structures is not a trivial one. The fine diameters of tubing and the low tensile strength of capillary column materials, such as fused silica, make the arrangement of capillary columns and of capillary connectors for the capillary tubes especially difficult. Although many methods and procedures for making such connections are possible, the connections generally require bonding to a conduit that has a circular cross-section. Suitable connection arrangements have been described in patents and applications such U.S. Pat. No. 5,692,078 as well as copending applications Ser. No. 60/065,712 and 60/065,711; both provisionally filed Nov. 14, 1997.

In the present state of the art for chromatography, capillary columns can have a larger sample capacity by increasing its bore and applying a thicker stationary phase, or it can have higher plate efficiency by reducing its bore diameter and using a thinner stationary phase. A way of getting both benefits simultaneously is to use a multi-capillary. A multi-capillary is a grouping of many capillaries all bundled together. This results in a Van Deemter curve that is relatively flat compared to conventional single capillary columns. The benefits of a multi-capillary have been known for several decades, but have not been commercially implemented because of the difficulties in manufacturing a multi-capillary using conventional glass capillary drawing techniques.

The current state of available capillary structures also detracts from the benefits of using capillary electrophoresis (CE). Perhaps the biggest impediment to wide scale use of capillary electrophoresis is the relatively small sample sizes that are provided by the use of single capillaries. There is a great need for more flow area to provide greater analyte recovery. The total internal volume of the capillary is typically less than 1 $\mu$L. This size results in a sample injection of usually less than 10 nL. For a sample containing 10 analytes, the total volume in each separated analyte is less than 1 nL, which is too small a fraction for most laboratory uses. Both liquid chromatography and gas chromatography frequently employ a mass spectrometer at the back end of a separation to determine analyte composition. The commonly minute volume of analyte recovered by CE methods leaves the mass spectrometer unable to resolve what the analyte is. The entrance of the buffer solution into the mass spectrometer and the need to have an electrical termination for the capillary column at the entrance to the ion chamber of the mass spectrometer compounds the problem of determining analyte composition with mass spectroscopy. Therefore the currently small amounts of recovered samples from CE separation push most detection equipment to or beyond their limits.

However, the performance of capillary electrophoresis (CE) begins to suffer when the diameter of most capillaries exceeds 75 microns. The 75 microns is not an absolute limitation, but the capillary diameter is dependent on the ion concentration of the buffer, applied voltage, the amount of gas contained in the ionic solution, the length of the capillary, etc. It has also been suggested that the high levels of power, i.e. voltage and current, dissipated in the capillary begins to exceed the capillary's ability to conduct away the resulting heat. Thus, as the ionic fluid becomes hotter, the desired quiescent conditions are lost and temperature runaways may result. Such runaways are believed to be responsible for non-reproducible separations.

Consequently, improved capillary structures could greatly benefit CE as well as other separation methods. For example capillary structures that could provide additional flow area for a sample without presenting problems of distribution and collection from multiple small capillaries would overcome problems of small sample recovery—one of the greater difficulties at this time with CE. Additionally, the problems of temperature runaway could be overcome by capillary structures that would provide suitable temperature control within a multiple capillary structure or a capillary structure having a relatively large capillary diameter for the ionic solution.

In particular regard to CE, it has been suggested that its performance may be enhanced by the use of multiple electrical fields at angles of 90° or 120° to the axial electrical field commonly associated with CE. The text "Practical Capillary Electrophoresis" mentions at page 126 the use of additional electric fields at different angles. Capillary structures that facilitate the introduction of additional electrical fields could provide an additional parameter for tailoring CE separations to the recovery of particular analytes.

U.S. Pat. No. 5,202,010 shows the use of an annular structure for improving detection of analytes recovered by CE . However, the annular structure is only used at the very end of the capillary to provide contact of an additional solution with the sample as it exits the capillary. In addition, the outer annular area shown in U.S. Pat. No. 5,202,010 is generally larger than capillary size.

It is a broad objective of this invention to provide capillary structures with improved versatility. A more specific object of this invention is to provide a single capillary tube that provides multiple capillary passages. Another specific object of this invention is to provide a single capillary tube that provides capillaries suitable for multiple functions. Another defined objective of this invention is to provide a single capillary tube containing capillary passages of different, but controlled sizes. A yet further object of this invention is to provide a single capillary tube that can provide multiple capillary passages for capillary electrophoresis. Yet another specific object of this invention is to provide a single capillary tube that has passages for heating or cooling fluids within the capillary tube or for imposing transverse electrical fields across the capillary tubes.

BRIEF SUMMARY OF THE INVENTION

This invention is a compound capillary that can provide different sizes and different configurations for central and outer passages to suit a variety of process applications. The capillary tube of this invention has a structure that supplies a central capillary size passage and at least one outer capillary sized passage. The outer passage may consist of a single semi-annular form passage way or multiple capillary size passages. At least one link extends through the structure to position the central capillary passage with respect to the outer capillary passage or passages.

The outer capillary passage may often take the form of a semi-annular structure. The term "semi-annular structure" refers to a broken annulus that, but for the connecting link to an outer capillary, extends essentially around the wall of the central passage. The only deviation from a completely annular structure is the link, or stand-off, that passes between the outer wall of the annulus and the inner wall that defines the central passage.

When not in a semi-annular form, several rows or rings of the outer capillary passages may surround the central passage way. More typically, multiple capillary passages located outside of the central passage will lie centered about the central passage along a single ring. In such an arrangement, links will extend radially in a spoke-like manner along a straight radial line to define capillary passages about the single ring.

Apart from improving CE and chromatographic separations, the compound capillary tube of this invention may serve a variety of functions that can find beneficial use in any application that passes fluids in small controlled quantities and adjusts the properties of the fluids. The differing area of the different passages may have substantial benefits, particularly for cooling small fluid steams. A larger passage diameter may be used in the center of the capillary tube for passing a cooling fluid at a relatively high mass flow rate through the central passage in comparison to the capillaries in the outer passage ways. The central passage may also be sized to simultaneously perform cooling as well as the introduction of an electric current. The channel may simply be made large enough to accommodate a wire and a cooling fluid simultaneously or an increased diameter central passage may receive a conductive coating along its interior while leaving enough space to the inside of the coating for the passage of a cooling fluid.

The different channels can be arranged functionally to hold different materials. The different materials include solids as well as fluids. As previously discussed, the channels may hold electrically conducting materials. Such materials can include conductive polymers as well as wires made from traditional metallic conductors. Given a sufficiently low viscosity, conductive polymers may be injected to fully occupy a central and/or outer passages.

The different channels can also hold different fluids such as coolant fluids as previously mentioned. By providing a central passage, the compound capillary facilitates the isolation of the central capillary for separately passing different fluids through the outer capillary area and the central passage. Distribution and collection manifolds may introduce or collect a fluid from the one or more outer passages while leaving an independent conduit for recovery of fluid from the central passage.

The central channel may have particular use in chromatographic separations where a heating wire passing through the central space may have advantages. It is also possible to use the structure to provide a miniature heat exchanger that has precise heat control. Heat control in the heating or cooling function is enhanced by minimizing the thermal mass of the capillary structure particularly between the central passage way and the passage or passage ways containing the fluid undergoing heating or cooling.

The improvements that this invention offers to CE are particularly important. The biggest improvement is perhaps an increase in sample size without the need to use less desirable large capillaries or to tackle the complex problem of connecting multiple capillaries that are not part of a monolithic structure. Where improved sample recovery is the objective, this can be met by a capillary structure of this invention that provides additional capillary area, particularly the arrangement that provides multiple uniform channels. The capillary electrophoresis applications of this invention will particularly benefit separations for a number of different materials.

In particular, CE has already drawn attention for the separation of DNA. DNA sequencers already utilize arrays of capillary passages and read the output with laser based fluorescence. By adding MS detection, it is possible to tag each extension product with a different discriminating tag. The sample sizes obtained through the use of this invention further facilitate the use of MS and will allow the tracking of up to 400 multiplex samples on the same capillary. Such improvements to DNA studies by CE may also permit extended study of adduct formation with polycyclic carcinogens. Thus CE may have particular usefulness in elucidating another mechanism of carcinogenesis as well as diagnostic tests. Along the same lines, it has been observed that the number of repeats in certain genes can increase the risk of cancer. The repeat number is clearly discernable by measuring the migration velocity from an electropherogram and can lead to tests for forms of cancer predisposition.

Other analysis methods that may benefit from the use of an improved CE are chiral analysis for isolating chiral drugs. These types of separation require a wide dynamic range in capacity and detection. A high linear dynamic range is possible to be achieved with the improved CE methods of this invention.

However, as mentioned above, channels of different size can offer special functional improvements to CE. The cooling function of separate cooling channels can overcome the Joule heating effects caused by the electrical current through the capillary tube. The arrangement may use the large central channel in the manner previously described for control of cooling. Additional benefits may result by the use of the outer ring of passage to conduct the cooling fluid while maintaining the ionic solution in a central passage. Precise control of the temperature will permit the use of a larger single capillary passage and thereby increase the recoverable sample. The ability to raise the central passage diameter above the typical 75 $\mu$m limitation arises by the elimination of the Joule heating which otherwise would create unacceptable band broadening of the detected analytes. Adjustment of the thermal mass between the heat exchange channel and the ionic fluid carrying-channel will improve the response time and the precision to which temperature may be controlled.

This invention also offers a significant advantage by providing a practical structure for introducing a transverse electrical potential in CE applications. As previously mentioned, the passages can contain wires or conductive fibers. In addition, the conductive fibers or wires may occupy selected outer passages so that a transient or non-uniform electrical field may be introduced transversely over the capillary passage to give further variation or sharper isolation of lo components in the achieved separation. In any event, the ability to extend a conductive wire or fiber in through central portion of the compound capillary will facilitate the use of selective control of a transverse potential over different axial sections of the capillary tube.

Accordingly, in one embodiment this invention is a tube having flow passages of capillary size. The tube has an outer wall surrounding an outer area that extends axially through the tube. The maximum dimension across a transverse section of the tube to the outermost points of the outer area does not exceed 2mm; preferably does not exceed 1mm and more preferably does not exceed 700 $\mu$m. An inner wall surrounds an inner area that extends axially through the tube and that has a maximum transverse dimension to its outermost points of 1300 $\mu$m, preferably 500 $\mu$m, and more preferably 100 $\mu$pm.

In another structural embodiment, this invention is a capillary tube having flow passages of capillary size. The tube defines an inner wall surrounding an inner area that extends axially through the tube and defines a central passage that has a maximum transverse dimension to its outermost points of 1300 $\mu$m, preferably 500 $\mu$m, and more preferably 100 $\mu$m. An outer wall surrounds the inner wall and defines an outer area that extends axially through the tube to define at least one flow passage. The configuration or the diameter of the outer passage differs from the inner passage. Preferably the capillary tube is also characterized by the ratio of the outer area to the inner area not exceeding 25.

In another embodiment, this invention is a method for selectively retaining microvoids in bodies formed by the elongation, in at least one direction, of heat flowable materials. The method starts with a dimensionally stable body that surrounds a fluid filled void space having an initial form. The method heats and elongates the heated body in at least one direction. During elongation fluid vents from the void space through a flow restriction as the body elongation reduces the dimension of the void space in a direction normal to the direction of elongation. The method allows recovery of the elongated body with the void space having a final form modified from the original form.

A more specific forming method forms micropassages in bodies that are formed by the axial drawing of heat flowable materials. The method again starts with a dimensionally stable body, wherein the body defines a plurality of initial passages that extend along a principle axis of the body. The body is heated and elongated by drawing it down along its principle axis. A restriction on the venting of gas is imposed from at least one of the initial passages to a degree that will prevent collapsing of the initial passage as drawing of the heated body elongates the initial passage. The method again allows recovery of the body in an elongated form with at least one reduced diameter passage that was formed by restricting the venting of gas from an initial passage.

In other method embodiments, this invention is a method for removing the voids generated when multiple capillaries are placed within a containing tube and then drawn to a smaller size. This method includes sealing of the distal end of individual capillaries while allowing the voids to vent to atmosphere during the process of drawing. This method can remove the voids generated when multiple capillaries are placed within an outer tube and when the volume of undesired void space is greater than 10% of the area of the capillary outer diameter.

In another broad method embodiment, this invention is a method for CE that uses a compound capillary tube having multiple passages. The compound capillary is formed with multiple passages by drawing the capillary structure from a drawing stock that defines the desired multiple passages.

In a more specific method embodiment, this invention is a method of separating analytes by capillary electrophoresis.

The method introduces a sample to an input end of a compound capillary tube, the compound capillary tube comprising a monolithic body defining a central capillary passage and one or more outer capillary passages. Each of the passages has a diameter of less than 2 mm, preferably less than 500 $\mu$m and more preferably less than 100 $\mu$m or a flow area of less than 1 mm$^2$ preferably less than 0.5 mm$^2$ and more preferably less than 0.1 mm$^2$. Either or both of the central and outer capillary passages may contain a sample for separation as part of an ionic solution. The method imposes an electrical potential over at least the axial length of at least a portion of the compound capillary tube between the input end of the capillary tube and a discharge end of the capillary tube. Analytes are recovered for detection or are detected directly at the discharge end of the compound capillary tube.

The following detailed description discloses additional objects, details, and embodiments of this invention.

DETAILED DESCRIPTION OF THE INVENTION

All of the compound capillary arrangements of this invention may be formed by drawing down an assembly of one or more smaller conduits surrounded by a larger outer tube until the diameter of the inner conduits has been reduced to the desired capillary size. The outer wall and the inner walls of the compound capillary assembly may be made from any material that is suitably formed into the required structure. Thus the resulting capillary structure has an operating temperature that is limited by the stability or transition temperature of the material and any stationary phase coated on the inside of the capillaries. Drawing techniques used for forming glass fibers and tubes lend themselves most readily to the production of the tube structure of this invention. Suitable glass materials include lead silicate, borosilicate, conventional glasses (soda lime silicate), and other forms of high purity silica such as quartz or fused silica. A particularly preferred glass material is an alumino-silicate.

Figure 1:
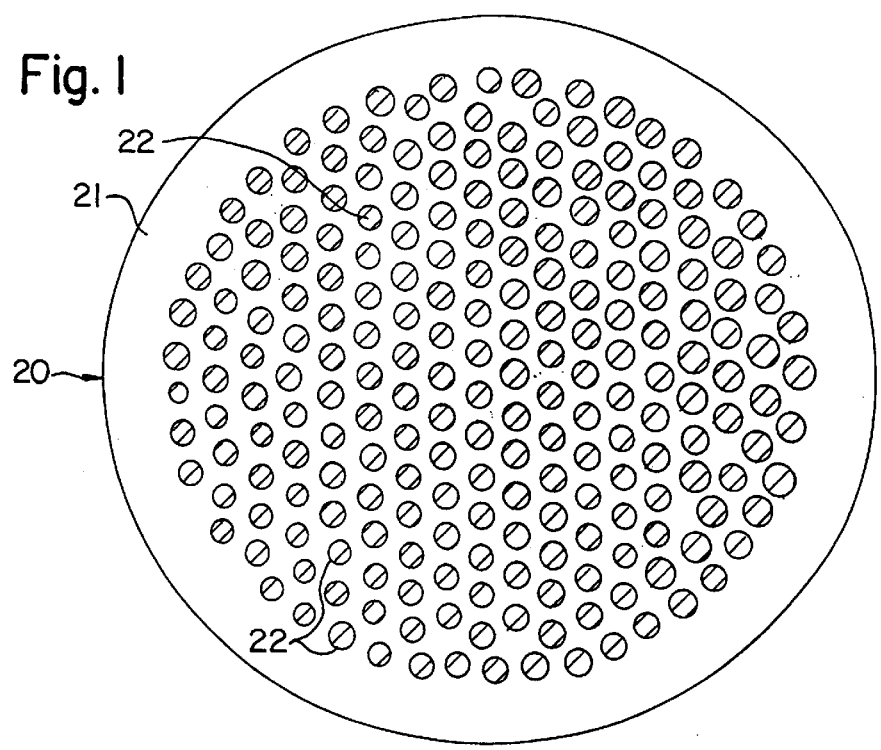
FIG. 1 is a transverse section across a compound capillary assembly having multiple uniformly sized capillaries.

Looking further at the capillary structures that can be arranged using this invention, FIG. 1 shows a nearly uniform arrangement of capillary passages in a compound capillary tube having an essentially round outer profile. This capillary arrangement provides a uniform array of individual capillaries having uniform diameters and an outer circular diameter. These capillary arrangements can be formed from ductile glass materials into an assembly that has an essentially round outer cross section and multiple capillary passages, typically of a size of 250 micrometers or less. This type of compound capillary assembly is characterized by multiple capillary sized passages of a regularly recurring shape, referred to as regular capillaries, that are formed together into a cohesive bundle by an outer wall having an essentially circular wall. Cohesion of the bundle refers to at least a portion of the regular capillaries sharing common internal walls that define the capillaries. The regularly recurring shape of the capillary cross sections is typically round but may take on oval and rectilinear shapes as well.

FIG. 1 shows the compound capillary structure 20 with virtually no irregular channels. The assembly of FIG. 1 provides a nearly perfect array of uniform capillaries 22 in a tube 21 having a circular outside cross section. FIG. 1 does show some variances in diameters between different capillaries and some minor ovaling of some capillaries. The minor irregularities will not have a significant impact on the application of the multi-capillary for separation operations. The ovality of the passages will have minimum changes on the flow-characteristics through such capillary passages. The small percentage capillaries passages with reductions in diameter will similarly have little negative affect on any separation results due to their small number and the regular overall shape of the capillary passages.

Where uniformity is desired, the open area defined by regular capillaries accounts for at least 20% of the total transverse cross-sectional area surrounded by the outer wall. The regular capillary passages will also have a substantially round cross-section and together typically account for not less than 90% of the total open area. Dimensions defining uniform regular capillary passages will preferably vary by no more than 15%.

The type of capillary arrangement shown in FIG. 1 may be produced by using an ordered packing of individual tubes for each passage in the capillary that is then drawn into a monolithic structure of reduced cross section. Although not always essential, the conduits that are drawn down in the compound capillary structure of FIG. 1 will preferably have round cross sections. It has been specifically found that, when forming a compound capillary with a plurality of internal capillary passages, minimizing the inner diameter of the outer containment tube for the number of capillary forming conduits contained therein dramatically increases the volume of regular capillaries formed during the drawing process. Prior to drawing, the conduits in the tube and conduit assembly will preferably have a diameter in a range of from 0.5 to 1 mm and a wall thickness of from 100 to 300 $\mu$m. A compound capillary of the type shown in FIG. 1 will usually contain at least 7 regular capillary passages. The thickness of the outer tube will usually average from 1 to 4 mm. The inner diameter of the outer tube will be determined by the number and outer diameter of the inner conduits. The most effective packing arrangement for the inner conduit has been found to be a number of circular rings of conduits that surround a central conduit. Jaycees Dutka, in Machinery Journal, October 1956, gives the maximum number of small circles that may be packed into a larger circle for a number of different packing arrangements. Based on these formulas, it has been found that for this invention the typical number of total passageways in a given number of passageway rings is best given by the formula for maximizing circles as presented in the foregoing reference. Therefore, where the desired arrangement for round conduits is as an assembly of rings about a central tube, the number of conduits in the assembly is determined by:

$$N=3n^2+3n+1;$$

where, N=the total number conduits, and
n=the number of rings of conduits around the central conduit.

Where all of the inner conduits have the same outer diameter, the preferred inner diameter of the outer tube is calculated in terms of a "K" factor defined by the above reference. Accordingly, the outer tube has an inner diameter "D" determined by the outer diameter "d" of the inner conduits where:

$$D=K*d$$

The factor K varies mathematically with the number of inner conduits. Values for K are set forth in the above reference. Examples of specific "K" values are set forth in Table 1 for arrangements that wrap rings of conduits around a central conduit.

TABLE 1

| # of inner conduits | I.D. of Outer tube |
|---|---|
| 2–7 | 3 |
| 8–13 | 4.465 |
| 13–19 | 5 |
| 20–31 | 6.292 |
| 32–37 | 7.001 |
| 38–43 | 7.929 |
| 44–55 | 8.212 |
| 56–61 | 9.001 |
| 62–73 | 9.718 |
| 74–85 | 10.166 |
| 86–91 | 11 |
| 92–97 | 11.393 |
| 98–109 | 11.584 |
| 110–121 | 12.136 |
| 122–127 | 13 |
| 128–139 | 13.166 |
| 140–151 | 13.490 |
| 152–163 | 14.115 |
| 164–169 | 14.857 |
| 170–187 | 15 |
| 188–199 | 15.423 |
| 200–211 | 16.100 |
| 212–223 | 16.621 |
| 224–235 | 16.875 |
| 236–241 | 17 |
| 242–253 | 17.371 |
| 254–262 | 18.089 |

The first several layers formed by the rings of conduits approximate a hex pack configuration, but as the layers of rings get larger (n>6), the layers appear to form a circle with some void space. Drawing of such a packed assembly produces a cross section that is more regular than a randomly packed cross section but not as free of defects as the capillary arrangement of FIG. 1. Such cross sections may still have considerable utility in a variety of process applications including those mentioned herein.

In order to reduce the occurrence of irregular capillaries, conduits with a thicker wall section are packed toward the outside of the assembly. Wall thickness of the conduits may be increased incrementally with increasing distance from the center of the tube. However, in some assembly draws, particularly as the number of packed conduits increases, minimum irregular channels were produced by uniformly increasing the wall thickness of all of the conduits in one or two of the outermost rows. The wall thickness selection of the conduits to minimize irregular channel formation will vary with the size and number of the desired capillaries and with the material of the assembly. The additional conduit wall thickness is preferably maintained by decreasing the inside diameter of the conduits. Surprisingly, it has been observed that the conduits with increased wall thickness tend to produce slightly larger capillaries than the capillaries produced by conduits with relatively thinner walls.

Forming the particular capillary structure of FIG. 1 relied on increasing the wall thickness of the last two or three rows of packed conduits to provide enough material to fill in the void space of the outer rows. The additional wall thickness of the outer walls reduces the void area of the total cross-sectional area surrounded by the outer wall to near zero such that the regular capillary flow area accounts for at least 95% of the total flow area through the multiple uniform passages of the capillary tube shown in FIG. 1. The surface tension of the outer containing tube and all of the enclosed conduits, when heated to their softening point, is sufficient to collapse the total assembly to a near void free cross section. Almost all of the conduits that start with thicker walls have the same inner diameter as the other inner tubes in the assembly. For a 217 capillary passages shown in FIG. 1, the outer rows 7 and 8 have increased wall thickness of 4 and 8 percent, respectively. The structure has 217 capillaries with diameters of about 40 $\mu$M in a capillary tube with an outer diameter of about 1.2 mm. The wall thickness chosen for the outer rows can be varied depending on the draw ratio and the temperature of the draw.

As an example of a forming technique for the capillary tubes of this invention, the multi-capillary shown in FIG. 1 was formed by the following method. The outer tube and 217 inner conduits had the following properties.

| | |
|---|---|
| outer tube I.D./O.D. | 12.7/15.2 mm |
| inner tube I.D./O.D. | 0.564/0.764 mm |
| glass material | aluminosilicate glass |
| glass melting point | 1120° C. |

To increase the uniformity, the wall thickness of the outer two rows of tubes were increased as described above. Whether used with uniform conduits or conduits with the varied thickness or diameters, the starting conduits have their top ends capped to inhibit gas flow in the tubing. This prevents the tubes from collapsing and forming a solid rod during the drawing process. The structure for the drawing stock is assembled one row of conduits at a time using glue or rubber bands to hold each row in place. The thicker outer walled tubing is added in the same manner. The assembly is mounted in the drawing tower and allowed to slowly equilibrate at the softening temperature of the glass. This begins to establish the surface forces on the initial part of the assembly and corrects for slight packing errors. The tip of the preform is then dropped and a tractor is used to draw the preform structure from the furnace. The drawing furnace was operated in the following manner:

| | |
|---|---|
| top feed rate | 1 mm/min |
| bottom feed rate | 190 mm/min |
| carrier gas flow (He) | 6 L/min |
| furnace temperature | 983° C. |

Capillary tubes of other sizes may be produced with varying numbers of uniform passages using the same formula and approach of increasing the walls of the last two or three rows in a progressive manner. Even if the number of rows are less than six, the outer rows must be increased in wall thickness to avoid a hex shaped outline and/or voids. The greater the number of rows, the more outer rows that need to have thicker walls.

A similar reduction in irregular capillaries can be achieved by using solid rods on the outer periphery of the bundle to produce a symmetric pattern. However, this technique seems to produce more anomalous behavior than the increased wall thickness of the outer rows and frequently distorts the inner and outer pattern of holes.

While not confirming any particular theory about the manner in which the method forms the tubes, it is believed that during the drawing process of the assembly surface tension of the outer structure forces the assembly to conform to its least geometric energy state. A symmetrical distribution of surface tensions of both the outer surface of the assembly and the inner surfaces of the bores coupled with bore pressurization to form a uniform pattern of holes with no void space.

A number of other forming techniques and material properties are important to obtaining the uniform multi-capillary structure. Drawing the structure from conduits that themselves have very uniform bores and walls enhances the uniformity of the resulting structure. Uniformity of the individual conduits may be enhanced by drawing the starting conduits down in several stages from large conduits. Uniformity of the resulting capillaries also improves as the alignment of the conduits in the drawing stock becomes more parallel.

Another important parameter when seeking to minimize irregular channel formation is temperature uniformity during the drawing process. It has been found that the drawing apparatus should not permit substantial temperature variations during the drawing operation. Temperature variations should be held to less than 5° C. degrees over the length of the draw.

Restricting the gas flow out of the tubes that undergo drawing is believed 40 to provide a key to the particularly useful method for forming the multiple passages in some of the capillary structures of this invention. When fabricating the capillary structures, assembling the various tubes into the drawing stock produces void volumes that extend down the length of the drawing stock. This invention in another form provides a method that preserves the desired void volumes that correspond to the tube bores while closing the void volumes that correspond to the area between the tubes. The selective closing of undesired void volumes while preserving desired void volumes is accomplished by restricting the flow of gas out of the tubes during the drawing process while leaving gas flow out the undesired void volumes unimpeded during the drawing process. Therefore, during the drawing process, restricted venting on desired void spaces prevents their collapse and overcomes the surface tension effects that would draw the material, now wetted by heating, into contact that would close the passage. Conversely, facilitating unrestricted venting from the undesired passages promotes closure and bonding of the wetted surfaces. Gas pressure maintained by restricted venting of some passages produces a transverse pressure on adjacent void volumes that further acts on these freely vented passage with a lateral flow of the body material that overcomes the usual symmetrical reduction of the cross section that occurs during most drawing processes.

This selective venting is usually provided by selectively sealing the desired void spaces at the end of the drawing stock that is fixed to the drawing tower and by leaving both ends of the undesired void spaces open at both ends of the drawing stock. Then during the drawing process gas from the desired voids can only leave through the bottom of the drawing stock while gas from the undesired voids can escape from either end of the drawing stock. Sealing the desired void spaces at the fixed end of the drawing stock is particularly effective since the fixed end usually retains its full cross section throughout the drawing operation while the drawn end undergoes dimensional reduction. Thus, the gas from the desired void volume can only escape through a single restricted opening while gas from the undesired void volume can escape from the large diameter opening provided by the initial size of the drawing stock and from any smaller opening at the bottom of drawing stock.

This venting control can be applied more generally to capillary formation and other structures. For example, it may be possible to produce a drawing stock having an enlarged cross section that replicates the cross section of the final drawn product. Using a die assembly to preform the drawing stock eliminates unwanted voids and only provides initial passages in a desired number and pattern. With the elimination of the undesired voids, gas flow may be restricted by using a valve to control the venting of gas from the upper ends of the void volume during the drawing process. Where the drawing stock contain unwanted voids and the desired void spaces are sealed at the upper end of the drawing stock, a vacuum may be imposed on the open ends of the undesired void volume to further induce its collapse.

These forming techniques may be applied to a variety of amorphous material or semi-crystalline materials. Suitable materials will have a difference between an annealing temperature and a melt temperature that maintains the material in sufficiently plastic state to permit forming. The material must still have a high enough viscosity to retain the form produced during the drawing operation until it is hardened by cooling. Crystalline materials are generally unsuitable for such operations since most undergo a phase change from a non-moldable solid to low viscosity liquid over a narrow temperature band.

This method can be used to form capillary structures with multiple passages that have unique properties that were unattainable in the prior art. For example, these techniques can reduce the wall thicknesses between capillary sized passages to less than 20 $\mu$m. Such ultra thin walls may separate passages having virtually unrestricted diameters to diameters as small as 10 nanometers. More typically, walls having thickness of 50 $\mu$m to 25 $\mu$m will separate passages having diameters of from 200 $\mu$m to 20 $\mu$m. Most common diameters for the separated passages will be 100 $\mu$m or less and more preferably 75 $\mu$m or less.

In addition to making thin walls between capillaries possible, the length to diameter ratios (L/d) of multiple passages contained in a single capillary tube may be dramatically increased. For passages having diameters of less than about 100 pm, preferably less than 75 $\mu$m and more preferably less than 50 $\mu$m, L/d's of at least 50,000 can be attained. It is further possible to obtain L/d's as large as one million and even 2 million by the above described forming methods.

In its most general form, these methods may selectively retain void volumes, particularly micro-void volumes, in bodies formed by the elongation, in at least one direction, of heat flowable materials. Such a general method would begin by fabricating a dimensionally stable body that surrounds a fluid filled void space. The void filled space would have an initial form. The body would undergo heating and elongation in at least one direction. Fluid in the void space would be vented through a flow restriction as the body undergoes elongation to reduce the dimension of the void space in a direction normal to the direction of elongation. The method would thereby provide an elongated body with the void space having a final form modified from the original form.

All of the compound capillary arrangements of this invention may be formed with similar techniques of drawing down smaller conduits that are surrounded at least by a larger outer tube and intermediate conduits or stand-offs. The drawing can continue in most cases until the diameter of the conduits has been reduced to the desired capillary size. It has been specifically found that minimizing the inner diameter of the outer containment tube for the number of capillary forming conduits contained therein can dramatically increase the volume of regular capillaries formed during the drawing process.

The diameter of the outer wall for most of the capillary arrangements will vary from 0.3 to 3.0 mm. Where an essentially round cross section is desired for the outer profile of the compound capillary, the variation in diameter taken along any two lines of direction within the substantially circular perimeter of the tube will preferably be less than 15%. The outer wall of the multi-capillary tube may be formed thicker than the internal walls separating the capillaries. The average thickness of the outer wall may exceed the average internal wall thickness by at least 50% and more often by a factor of 2. The outer wall may also be made of a different material than the inner walls. Complete cohesion of the wall between capillary passages is not necessary, but preferably at least 50% of the internal wall volume between adjacent capillary passages is integrally bonded. The maximum dimension of the regular capillaries does not exceed 250 µm and preferably does not exceed 60 µm. The minimum dimension of the capillaries to function in any application is usually 2 µm, although for some applications the capillaries may be as small as 2 nanometers.

Figure 2:
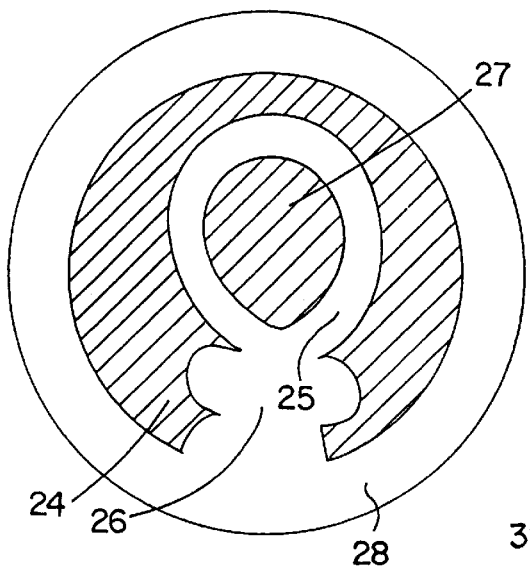
FIG. 2 is a transverse section across a compound capillary assembly of this invention showing an annular outer area.

FIG. 2 depicts an actual cross-section for a compound capillary of the type having the outer area in the form of a partial annulus 24 and a central passage defined by an inner wall 25. A radially extending link 26 serves as a stand-off that fixes and ideally centers the central passage 27 with respect to an outer wall 28 that defines the outside of outer passage 24. The partial annulus 24, also referred to as a semi-annular form, surrounds essentially all of the central passageway and the inner wall 25. The term "surrounds essentially all" will refer to the link or stand-off occupying a sector of the annulus having an included angle of less than 90°, preferably less than 70° and more preferably less than 45°.

This type of structure may again be formed by a drawing process. The stand off or link portion of this compound capillary is typically made using three pieces of flat glass— all of the pieces of glass having a starting size of 1–3 mm in width and 1–4 mm in height. The complete stand-off is formed by laying the flat pieces on top of each other inside a larger tube. The standoff pieces will usually extend down the entire length of the outer tube to provide a continuous link or stand-off, however the standoff pieces could be staggered to provide an intermittent stand-off where desired. Lastly, a smaller tube, ordinarily 50% smaller, is placed on top the stack of plates that form the stand-off. Once arranged, the whole assembly undergoes annealing at suitable conditions, such as 865° C. for thirty minutes to bond the assembly in preparation for drawing. Sealing of the tubes at the end of the assembly has been found to be unnecessary for drawing this tube configuration. After it has cooled to room temperature the bonded assembly is placed in a drawing tower and drawn under suitable drawing conditions. Preferred drawing conditions include the following:

| | |
|---|---|
| Furnace temperature | 1000° C.; |
| Top feed rate | 6 mm/min; |
| Bottom feed rate | 2 m/min; and, |
| Carrier gas flow (He) | 6 L/min. |

Figure 3:
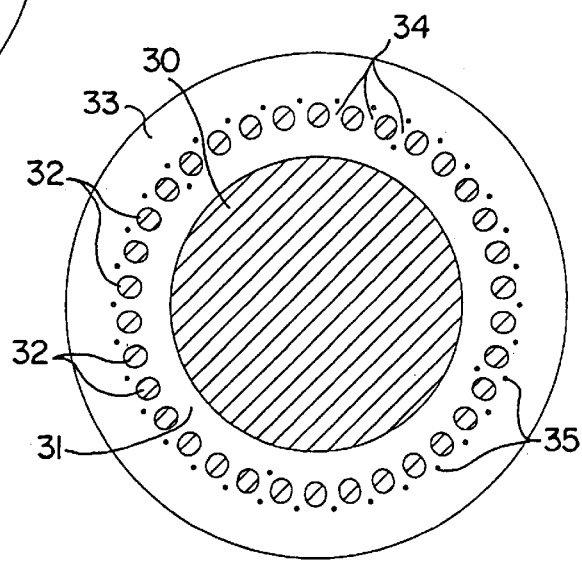
FIGS. 3 is a transverse cross-sections showing compound capillaries having the outer area divided into a ring of individual capillary passages.

FIG. 3 shows a cross section of the compound capillary where a plurality of capillary passages occupies the outer area. The Figure shows a central passage 30 surrounded by an inner wall 31 and a plurality of relatively uniform capillary passages 32 occupying an outer area between the outside of inner wall 31 and an outer wall 33. A series of spoke-like links 34 provide integral connections that serve the dual purpose of separating passages 32 and of fixing the inner wall with respect to outer wall 33. FIG. 3 does show minor irregularities in the form of minute open passages 35, located near the outer wall 33. These minute openings should not detract from the use of these compound structures in most applications and may be eliminated if desired by adjustment of the starting tube diameters and thickness in the forming process. FIGS. 1–3 do not show larger irregularities and broken channel sections that would normally appear in actual micro-graphs since these are attributable to damage sustained when preparing the capillary samples to take micro-graphs.

This form of compound capillary may be produced by again drawing an assembly of glass conduits down the desired size. Assembly of the drawing stock starts with the selection of an outer tube having an outside diameter of X and a wall thickness of W. A series of intermediate tubes, for forming the plurality of outer capillary passages, is then selected. The intermediate tubes should have an diameter Y that is selected to provide a relatively tight packing of the tubes against the inner diameter of the outer tubes. The diameter Y generally falls in a range of 0.5 mm to 4 mm. A third tube with a diameter Z acts as an inner tube and provides the inner wall. Diameter Z is set by the following relationship:

$$Z=X-2W-2Y.$$

The inner tube is then inserted into the center of the ring of outer tubes. The bundle of inner and intermediate tubes is inserted into the outer tube. A shrink wrapping is placed around the bundled ends of inner and intermediate tubes. Application of heat to the shrink wrap with a heat gun or other relatively low temperature heating device binds the inner and intermediate tubes into a tight fit. The very ends of tubes Y and Z are then heated until they totally close and make a complete seal. Once shrunk together, a propane torch or other relatively high heat device is used to close the ends of the inner and intermediate tubes until a complete seal is formed. The end of the outer tube should not be bonded to the inner and intermediate tubes in this process. In order to allow sealing of inner and intermediate tubes without burning the shrink wrap of bonding of the outer tubes during sealing of the inner and intermediate tube ends, the ends of the inner and intermediate tubes protrude approximately 2 inches past the end of the outer tube. After the drawing assembly has cooled, it is placed in a drawing tower and drawn as follows under the same condition as previously described for the tube of FIG. 2. By this method, the tubes in FIGS. 3 may be formed to provide the desired capillary size of both inner and outer passages.

Once formed, an outer sleeve may surround the compound capillary to provide additional support and structural integrity or other functional inputs. Metallic materials will work well as outer sleeves for purposes of structural support, heating or cooling, and electrical or magnetic input. An especially beneficial arrangement may shrink a metallic sleeve around a glass multi-capillary assembly to compress the tube into the sleeve. An arrangement of this type may provide the needed structural support for imposing the necessary ultra-high pressures that are required to push many fluids through capillaries that approach 2 $\mu$m in diameter.

Figure 4:
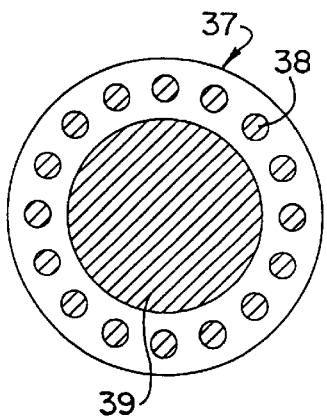
FIGS. 4–6 are schematic diagrams showing idealized cross-sections of FIGS. 2–3.
Figure 5:
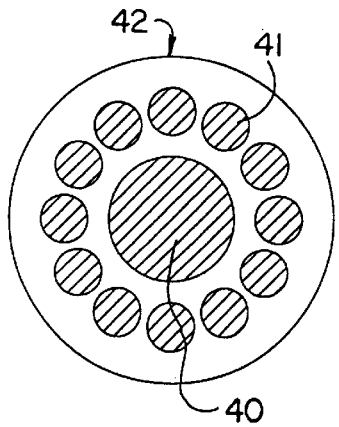
Figure 6:
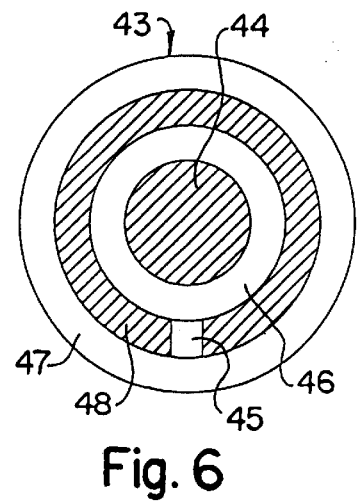

FIGS. 4–6 show idealized sections for the tubes of FIGS. 2–3. The size and arrangement of the central and outer passages may be varied in accordance with the intended functions of the compound capillary passages. For example, in the case of a compound capillary that provides an internal cooling function, FIG. 4 shows a compound capillary 37 with a ring of separate capillary passages 38 surrounding a central capillary 39. The relative sizing of the capillaries in FIG. 4 generally suits the passing of a cooling fluid through the outer passages 38 and a sample stream through the relatively large central passage 39. The compound capillary 42 of FIG. 5 reverses the relative passage sizing and surrounds a relatively small central passage 40 with a ring of relatively large outer capillary passages 41. FIG. 6 shows a compound capillary 43 with a semi-annular outer passage 48 that surrounds a central passage 44. As previously described, a stand-off 45 positions an inner tube 46 with respect to an outer tube 47. Relative sizing of the annular and central passages may be adjusted as desired by increasing or decreasing the size of the inner tube 46 during the forming process. Therefore, outer passage 48 and central passage 44 may have relative sizing that will accommodate the passing of cooling fluid or sample fluid through either passage.

Similar adjustments in sizing may be employed when using compound capillary structures to retain heterogeneous solids in some of the capillary passages. Conductive material such as traditional wires or conductive polymers have been given as example of functional solids that may be located in the passageways. In the case of wires, insertion of the wire will usually occur at the time of drawing but may follow formation of the compound capillary structure. Accordingly, a capillary, through which a wire will pass, typically has an average diameter about 10% greater than the maximum diameter of the wire to accommodate sliding of the wire and variations in the diameter of the capillary passage that receives the wire. In most cases, the wire will pass through a relatively large central passage such as that shown in FIG. 4 or a large central capillary passage formed in the annular arrangement of FIG. 6. Central wires in these arrangements may be used for inducing electrical currents or as resistance heating elements. It is also possible to provide a ring of relatively large passages around a smaller central passage as shown in FIG. 5. Wires or other conductive material may again fill essentially all or a portion of passages 41. A ring or wires is anticipated to provide the most benefit in resistance heating applications. Where used to induce magnetic or electrical fields, as in new electrophoresis methods, the wires will usually occupy the central passage.

Figure 7:
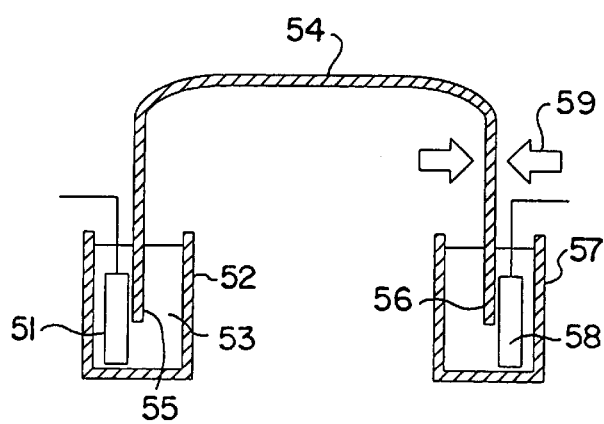
FIGS. 7 and 8 are schematic representations of apparatus arrangements for capillary electrophoresis.

The standard laboratory arrangement for conducting simple capillary zone electrophoresis (CZE) is schematically shown in FIG. 7. FIG. 7 shows a positively charged electrode 51 extending into a reservoir 52 that retains an ionic solution 53 or buffer. A capillary tube 54 in the shape of an inverted U has an input end 55 that extends into reservoir 52. A discharge end 56 of capillary 54 extends into a reservoir 57 that retains a cathode 58. Capillary 54 is filled over its length with ionic solution by a suitable filling method such as the application of a vacuum at one end of the capillary to draw the buffer through the capillary passage. The sample may be introduced into the capillary by a variety of methods known to those skilled in the art. Hydrodynamic injection is routinely employed wherein the sample is dispersed in the buffer solution and a momentary flow is produced by briefly raising the reservoir containing the sample or applying a positive pressure vacuum to reservoirs 52 and 57, respectively. After injection of the sample into the input end of the capillary, application of a voltage potential, usually on the order of 10,000 to 30,000 volts, at relatively small amperage of from 20 to 100 $\mu$A creates a flow of electrons through capillary 54. In simple operations the electron flow drags different components of the sample through capillary tube 54 at different rates depending upon mobility of each solute. A detector 59 near the discharge end of capillary 54 detects the characteristic properties of the separate analytes that pass by the detector at different times. UV absorbance detectors are by far the most popular for HPCE, in particular diode array detectors are especially popular.

In accordance with this invention capillary tube 54 may comprise any of the compound capillaries as previously described. The compound capillary of this invention will greatly increase the quantity of analyte throughput and, therefore, can provide recovery rates up to 50 to as 250 $\mu$liters/minute by the addition of capillary passage area. These increases are obtainable whether the capillary area is increased by the addition of more uniformly sized capillaries, the use of a single enlarged capillary passage or the provision of an annular capillary passage.

Figure 8:
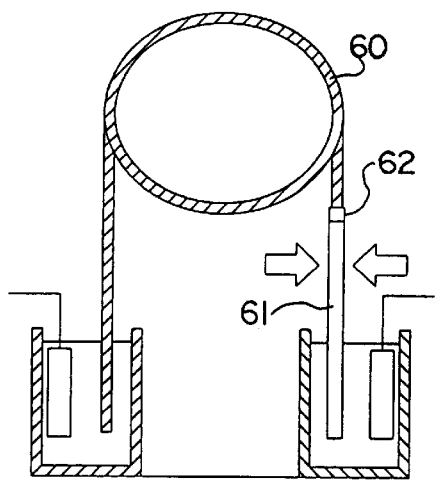

FIG. 8 shows an arrangement for CE that is similar to that shown in FIG. 7, but particularly suited for use with multiple uniform capillaries. FIG. 8 differs by the use of the capillary in a wound arrangement 60 and, more importantly, in the connection of the delivery end of the capillary 60 with a detection tube 61. Detection tube 61 overcomes the-detection problems associated with the many capillaries within the structure disrupting the lateral radiation beam of a UV or other optical detector. Detector tube 61 overcomes this problem by placing a glass sleeve, typically a fused silica tube, over the end of the compound and dimensioning the bore of the tube to correspond to the total bore area of passages that contain buffer solution. This also permits a larger cross sectional area for the detector beam which improves the lower limit of detection. Detection tube 61 thus provides a low volume transition for collecting the sample into a single capillary. The transition provides a tapered section 62 that begins at the attachment end with an internal cross-sectional area that corresponds roughly to the outside diameter of the compound capillary. The final cross sectional area at the end of the section 62 and through tube 61 is considered to be about equal when the area of the single passage of the detection channel and the combined area of compound capillary passages that contain the buffer solution differ by less than 25%, preferably less than 15% and more preferably less than 5%.

When using multiple capillary passages, there is no specific tolerance between the bores that is acceptable. For satisfactory performance the compound capillary must have the individual bores within the structure closely matched in size. If one bore is substantially larger than the other bores, the larger bore will conduct more current resulting in it getting hotter than the other bores and thus causing it to further increase in temperature thereby resulting in a runaway condition. The tolerance on variation between passages is generally dependent on the values of the run parameters during a particular use of the compound capillary. Thermal runaway is dependent on many parameters but, if the parameters of voltage and buffer concentration are backed off sufficiently, a stable separation will result. Considering a single capillary with a 75 micron bore, if thermal runaway occurs at a voltage of 30,000 volts per meter and at a buffer concentration of 0.1N, then backing down to 20,000 volts and a 0.05N buffer concentration will result in stable operation for that same capillary. Generally, if the tolerance of the bores of the compound capillary are within 5% of each other, there is little problem of thermal runaway for this latter example using a compound capillary. But as the inter-bore variation increases, for example by 10%, the possibility of thermal runaway becomes greater. Only when the parameters are "pushed" to get maximum performance does this become an issue for a capillary with multiple passages. The same is true for a single capillary but with suitably corresponding sample limitations.

Figure 9:
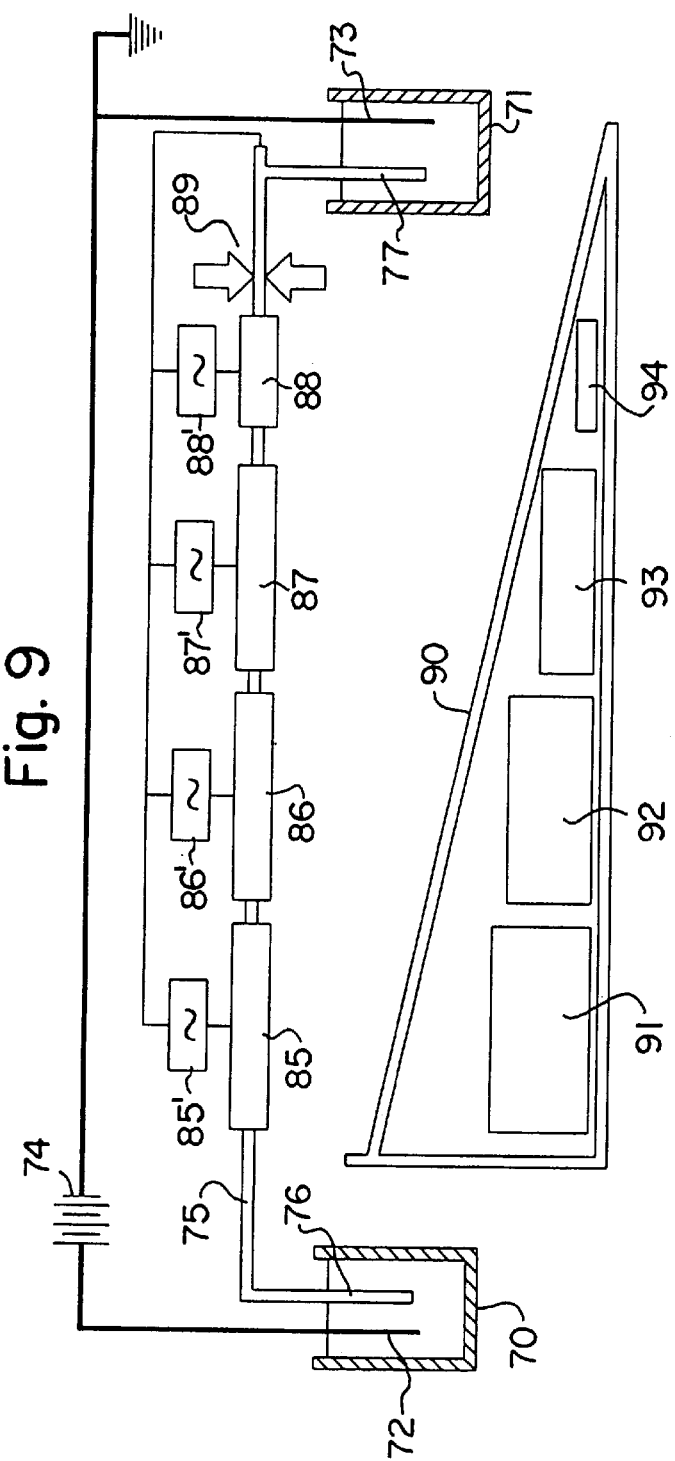
FIG. 9 is another schematic CE arrangement that imposes transverse electrical fields across axial sections of a capillary tube to impose dynamic transverse electrical fields.
Figure 10:
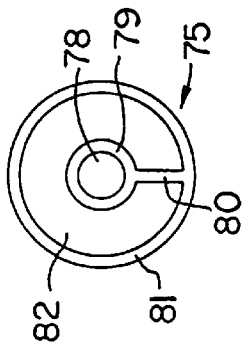
FIG. 10 is an idealized cross-section of a compound capillary retaining a wire in a central passage.

FIG. 9 shows a CE arrangement similar to that of FIGS. 7 and 8, but differing in the use of central capillary for an alternate function. In this arrangement, separate reservoirs of buffer solution 70 and 71 retain an anode 72 and a cathode 73, respectively. A voltage source 74 provides an electrical potential between reservoir 70 and 71. Ionic fluid occupies a compound capillary 75 that has an input end 76 in reservoir 70 and a delivery end 77 in reservoir 71. A detection apparatus analyzes the sample components as they pass through the end of the capillary. As shown in FIG. 10 the compound capillary 75 has a central passage 78 defined by an inner capillary conduit 79. A radial link 80 fixes the position of inner conduit 79 within an outer capillary conduit 81. Outer capillary conduit 81 defines a semi-annular space 82 to its inside. Link 80 and inner capillary conduit 79 define the interior borders of semi-annular space 82.

Central passage 78 retains a wire that provides a radial electric field across the transverse section of compound capillary 75. The wire is preferably a high conductivity metal such as gold. The wire operates in conjunction with a series of electrically conductive bands 85, 86, 87, and 88 that each surround the outside of the compound capillary. Each band provides a conductive segment that receives a voltage source with its own isolated oscillator. The bands may be provided by coating the outer tube with a conductive coating such as a tin oxide (SnO). The electrical field created by each oscillator is isolated from the longitudinal field and to each other by individual isolation transformers 85',86', 87' and 88'. The oscillators, however, have a common ground in the center of the capillary. The ground is brought out at the right beaker and individually referenced to each oscillator but not to the high voltage terminal of the longitudinal field or its ground.

Coating the outer tube with a conductive coating and adding a ground wire through the central passage provides the needed elements to generate a radial electric field within the open annular section that transports the solute. The longitudinal electric field is used in the classic sense to generate a longitudinal flow of the buffer within the annular capillary for modulation of that by a radial field. By segmenting the outside conductive coating, several different radial fields can be applied in an independent manner. Knowing the location of the separating sample plug at any given time as it propagates through the capillary allows dynamic imposition of the radial electric fields to enhance a given separation. The maximum intensity of the radial field will usually be less than the axial field and usually less than 1,000 volts. Voltages will typically oscillate at a frequencies in the range of 1 to 100 Hz.

The graph in FIG. 9 shows a plot of the voltage along the length of the capillary. The top line 90 shows the voltage of the axial field decreasing linearly with increasing resistance through the buffer solution. Bars 91–94 represent the absolute magnitude of the applied radial fields over the segments 85–88, respectively. In addition to changing magnitude, the radially applied voltages will ordinarily oscillate between positive and negative values. FIG. 9 shows one radial voltage pattern where the absolute magnitude of the oscillating fields decreases in succeeding segments along the length of the capillary. Of course, any number additional segments with any pattern of oscillating or steady fields may be applied radially or at any transverse angle.

The radial fields may be used to modify the cross section of an electro-kinetically propagated molecule within the annulus of the capillary. Long, thin polar molecules will be most affected while small molecules will be less influenced by the radial field. This phenomenon is similar to what occurs in slab gel electrophoresis where the separation of DNA molecules uses a dynamic second field to relax the extended molecule into a unique shape that is related to its charge and length properties. In the annular capillary the radial field alters the shape or cross section (in the axial direction) of the molecule propagating within the annulus. Each unique molecule will have a specific mobility within the buffer for a given applied axial electric field and a radial field of a given intensity and frequency. A single axial field only stretches the molecule so that different length molecules have the same frontal cross section and therefore the same mobility, while the axial field affects molecules of different lengths differently resulting in varying frontal cross sections and therefore different mobilities. This differentiating property will be similar for long, polar molecules whether the solute is a low viscosity buffer or a cross linked gel.

The dynamic radial field has several advantages over the stretching effect of the axial field alone and offers numerous possibilities. The radial field will cause the molecule to bend in the radial direction or, if the radial field changes rapidly, will cause the molecule to form into a sine wave. The molecule will resonate at a specific frequency determined by the length of the molecule, the location of polar constituents along the molecule's length, the viscosity of the medium, and the pH of the medium. The resonation, in turn, generates a maximum cross section as viewed in the longitudinal direction. It is concluded that the greater the cross section of the molecule, the greater the resistance to flow; and the shorter the molecule, the higher the resonant frequency: and more branching will result in a higher frequency of resonance, etc. For a limited number of axial segments (<10), each segment could be tuned to a specific frequency to delay a particular analyte within the sample. For many closely spaced segments a continuously changing (frequency and position) traveling wave could follow the sample plug and over many segments "coax" closely related analytes apart. It is possible to vary the longitudinal field and thereby provide an additional degree of freedom.

Another variation includes the addition of chiral stationary phases to the wall of the annulus to allow for additional degrees of separation. Chiral molecules are typically long and have a dipole along their length. Either the chiral stationary phase or the electric fields or both can provide a unique orientation for many chiral molecules. Suitable stationary phases may also be used to separate small molecules where the multiple electric fields will have the greatest impact on the larger molecules.

What is claimed is:

1. A tube having flow passages of capillary size comprising:
   an outer wall surrounding an outer area that extends axially through the tube and the maximum dimension across a transverse section of the tube to the outermost points of the outer area does not exceed 2 mm,
   an inner wall surrounding an inner area that extends axially through the tube and that has a maximum transverse dimension to its outermost points of 1300 μm; and,
   at least one link extending along a radial line from the inner wall to the outer wall and rigidly connecting the inner and outer walls to fix the position of the inner area with respect to the outer area.

2. The tube of claim 1 wherein the inner area provides an open central channel that extends through the center of the tube.

3. The tube of claim 1 wherein the inner area contains an electrically conductive material that extends through the center of the tube.

4. The tube of claim 1 wherein the outer area comprises an open channel having a semi-annular shape and the link extends across the open channel at a single location.

5. The tube of claim 1 wherein the inner and outer walls have an annular profile.

6. The tube of claim 1 wherein a series of links defines a plurality of flow passages that occupy the outer area and surround the inner wall.

7. The tube of claim 6 wherein the inner wall, the outer wall, and the links define the plurality of flow passages in the form of capillaries having a diameter of less than 300 μm that surround the inner wall.

8. The tube of claim 7 wherein the outer wall has a substantially circular profile and the variation in diameter taken along any two lines of direction within the substantially circular perimeter or the variation in diameter taken along any two lines of direction within the substantially circular cross section of each flow passage varies by not more than 15%.

9. The tube of claim 7 wherein the variation between diameters of the flow passages varies by no more than 15%.

10. The tube of claim 1 wherein the diameter of the flow passages does not exceed 60 micrometers.

11. The tube of claim 1 wherein the outer wall and the inner walls are formed from the same material.

12. The tube of claim 1 wherein the outer wall and the inner wall and the link are formed from a glass comprising an alumino-silicate.

13. The tube of claim 1 wherein the outer wall has a diameter of less than 0.5 mm.

14. The tube of claim 1 wherein the inner area or the outer area retains a heating element.

15. A capillary tube having flow passages of capillary size comprising:
   an inner wall surrounding an inner area that extends axially through the tube and defines a central passage and that has a maximum transverse dimension to its outermost points of 1300 μm; and,
   an outer wall surrounding the inner wall and defining an outer area that extends axially through the tube to define at least one flow passage, wherein the configuration or the diameter of the outer passage differs from the inner passage.

16. The capillary tube of claim 15 wherein the ratio of the outer area to the inner area does not exceed 25.

* * * * *